(12) United States Patent
Yamada (10) Patent No.: US 10,712,328 B2
(45) Date of Patent: Jul. 14, 2020

(54) ANALYSIS DEVICE

(71) Applicant: TOSHIBA MEMORY CORPORATION, Minato-ku, Tokyo (JP)

(72) Inventor: Yuji Yamada, Mie (JP)

(73) Assignee: TOSHIBA MEMORY CORPORATION, Tokyo (JP)

( * ) Notice: Subject to any disclaimer, the term of this patent is extended or adjusted under 35 U.S.C. 154(b) by 116 days.

(21) Appl. No.: 15/449,384

(22) Filed: Mar. 3, 2017

(65) Prior Publication Data

US 2018/0088100 A1    Mar. 29, 2018

(30) Foreign Application Priority Data

Sep. 23, 2016 (JP) .................................. 2016-185393

(51) Int. Cl.

| | |
|---|---|
| *G01N 33/20* | (2019.01) |
| *G01N 23/20* | (2018.01) |
| *G01N 23/223* | (2006.01) |
| *G01N 1/40* | (2006.01) |
| *G01N 1/38* | (2006.01) |
| *G01N 1/32* | (2006.01) |
| *G01N 23/20033* | (2018.01) |
| *H01L 21/66* | (2006.01) |
| *H01L 21/67* | (2006.01) |
| *G01N 33/00* | (2006.01) |

(52) U.S. Cl.
CPC ............... *G01N 33/20* (2013.01); *G01N 1/32* (2013.01); *G01N 1/38* (2013.01); *G01N 1/4022* (2013.01); *G01N 23/20033* (2013.01); *G01N 23/223* (2013.01); *G01N 2001/383* (2013.01); *G01N 2001/4027* (2013.01); *G01N 2033/0095* (2013.01); *G01N 2033/0096* (2013.01); *H01L 21/67051* (2013.01); *H01L 21/67276* (2013.01); *H01L 22/12* (2013.01)

(58) Field of Classification Search
None
See application file for complete search history.

(56) References Cited

U.S. PATENT DOCUMENTS

| | | | |
|---|---|---|---|
| 6,790,376 B1* | 9/2004 | Markle | ............. H01L 21/67253 216/59 |
| 2003/0043963 A1* | 3/2003 | Yamagami | ........... G01N 23/223 378/44 |

(Continued)

FOREIGN PATENT DOCUMENTS

| | | |
|---|---|---|
| JP | H09-145569 A | 6/1997 |
| JP | 2001-153768 A | 6/2001 |

(Continued)

*Primary Examiner* — Kathryn Wright (74) *Attorney, Agent, or Firm* — Foley & Lardner LLP (57) ABSTRACT

An analysis device includes a vapor phase decomposition unit, a heating unit, an evacuation unit, a recovery unit and an analysis unit. The vapor phase decomposition unit performs vapor phase decomposition of a first film on a substrate. The heating unit heats the substrate. The evacuation unit evacuates gas in the heating unit to an outside of the heating unit. The recovery unit supplies liquid on a front surface of the substrate, moves the liquid on the front surface of the substrate, and recovers the liquid. The analysis unit analyzes contents of the liquid.

15 Claims, 6 Drawing Sheets

(56) References Cited

U.S. PATENT DOCUMENTS

| | | | | |
|---|---|---|---|---|
| 2006/0057804 A1* | 3/2006 | Saito | ................... | H01L 21/3065 |
| | | | | 438/254 |
| 2013/0244349 A1* | 9/2013 | Yamada | ................. | H01L 22/12 |
| | | | | 438/14 |
| 2016/0013053 A1* | 1/2016 | Ashihara | ........... | H01L 21/02164 |
| | | | | 438/778 |

FOREIGN PATENT DOCUMENTS

| | | | | |
|---|---|---|---|---|
| JP | 2004-028787 A | 1/2004 | | |
| JP | 2013-190403 A | 9/2013 | | |
| JP | 2014-041030 A | 3/2014 | | |
| WO | WO-2014157210 A1 * | 10/2014 | ....... | H01L 21/02164 |

* cited by examiner

ANALYSIS DEVICE

CROSS-REFERENCE TO RELATED APPLICATION

This application claims the benefit of and priority to Japanese Patent Application No. 2016-185393, filed Sep. 23, 2016, the entire contents of which are incorporated herein by reference.

FIELD

Embodiments described herein relate generally to an analysis device.

BACKGROUND

Metal impurities existing in a semiconductor thin film cause degradation of a breakdown voltage and crystal defects, and degrade characteristics of a semiconductor device. The metal impurities existing in the semiconductor thin film can be analyzed by using a vapor phase decomposition (VPD) method. However, improvements in such metal impurities analysis remain desired.

DETAILED DESCRIPTION

The metal impurities existing in the semiconductor thin film can be analyzed by using a vapor phase decomposition (VPD) method. In a case where a film containing nitrogen or a thick (for example, 10 nm or greater) silicon oxide film is analyzed, a silicon compound (or decomposition product) such as ammonium fluorosilicate ($(NH_4)_2SiF_6$), in addition to the metal impurities, may remain in a chemical liquid. The chemical liquid can be recovered by scanning a substrate, after the vapor phase decomposition is performed. Since the decomposition product makes metal analysis difficult, thermal decomposition is considered which is performed by heating a substrate after the vapor phase decomposition is performed.

However, there is a concern that the decomposition product which is thermally decomposed when being heated is attached to and deposited on an inner wall of a container, and thereafter, the decomposition product is dropped on a substrate. In this case, a problem occurs in which metal impurities are hard to be analyzed by the dropped decomposition product.

An example embodiment provides an analysis device which can analyze easily and accurately metal impurities in an analyte film.

According to some embodiments, an analysis device may include a vapor phase decomposition unit, a heating unit, an evacuation unit, a recovery unit, and an analysis unit. In some embodiments, the vapor phase decomposition unit may perform vapor phase decomposition of a first film on a substrate. The heating unit may heat the substrate. In some embodiments, the evacuation unit may evacuate gas in the heating unit to an outside of the heating unit. In some embodiments, the recovery unit may supply liquid on a front surface of the substrate, move the liquid on the front surface of the substrate, and recover the liquid. In some embodiments, the analysis unit may analyze contents of the liquid.

Hereinafter, example embodiments of the present disclosure will be described with reference to the drawings. The embodiments described herein do not limit the present disclosure.

Figure 1:
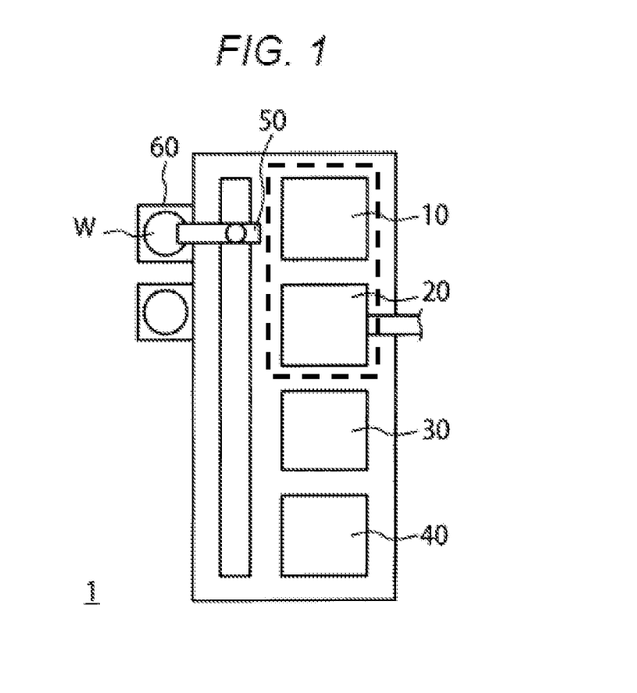
FIG. 1 is a schematic plan view illustrating an example of a configuration of an impurity analysis device according to some embodiments.

FIG. 1 is a schematic plan view illustrating an example of a configuration of an impurity analysis device 1 according to some embodiments. In some embodiments, the impurity analysis device 1 (Hereinafter, referred to as an "analysis device 1") can analyze metal impurities included in a material film that is an analysis target formed on a substrate by using, e.g., vapor phase decomposition (VPD). In some embodiments, the analysis device 1 may be an automatic analysis device which automatically performs a process from vapor phase decomposition to analysis. In some embodiments, the analysis device 1 may analyze the metal impurities by using, for example, any one of a total reflection X-ray fluorescence (TXRF) method, an inductively coupled plasma-mass spectrometry (ICP-MS) method, and an atomic absorption spectrometry (AAS) method.

In some embodiments, the analysis device 1 includes a vapor phase decomposition unit 10, a heating unit 20, a recovery unit 30, an analysis unit 40, and a transport unit 50. In some embodiments, each of the vapor phase decomposition unit 10, the heating unit 20, the recovery unit 30, and the analysis unit 40 includes a chamber, and can contain a substrate W in the chamber. In some embodiments, the transport unit 50 includes a robot hand, and can transport the substrate W between a substrate container 60, the vapor phase decomposition unit 10, the heating unit 20, the recovery unit 30, and the analysis unit 40.

In some embodiments, the vapor phase decomposition unit 10 can perform vapor phase decomposition of a material film (referred to as a "first film") on the substrate W by using processing gas, dissolve metal impurities existing in the material film together with a material film on a front surface of the substrate W, and retain the material film and the metal impurities on a front surface of the substrate W. More detailed configuration of the vapor phase decomposition unit 10 will be described with reference to FIG. 2 below.

In some embodiments, the heating unit 20 can heat and dry the substrate W. In some embodiments, a hot plate may be provided in the chamber of the heating unit 20, and the substrate W may be mounted on the hot plate to be heated. More detailed description on the heating unit 20 will be described with reference to FIG. 3A and FIG. 3B below.

In some embodiments, the recovery unit 30 can supply a recovery solution onto the front surface of the substrate W from a nozzle, and move the solution from the nozzle to the center of the substrate W, while retaining and rotating the substrate W by using, e.g., a rotary retention unit. Thereby, in some embodiments, an object to be measured (e.g., metal impurities) exiting on the front surface of the substrate W can be recovered into the solution. In some embodiments, in a case where the analysis unit 40 which will be described below is a TXRF analysis device, a heating unit such as a lamp may be provided in the recovery unit 30, and the solution into which the object to be measured may be recovered can be heated and dried. More detailed configuration of the recovery unit 30 will be described with reference to FIG. 4 below.

In some embodiments, the analysis unit 40 can analyze contents of the material film incorporated into the recovery solution. For example, in a case where an X-ray fluorescence analysis is performed, the analysis unit 40 can analyze the object to be measured by irradiating the object to be measured on the substrate W with an X-ray. In some embodiments, the analysis unit 40 may be a total reflection X-ray fluorescence (TXRF) analysis device which analyzes metal contamination on a front surface of the substrate by making the X-ray be incident on the front surface of the substrate at an extremely low angle and using the X-ray which is totally reflected from the front surface of the substrate. In some embodiments, the analysis unit 40 may be a device which can analyze a metal, and may be a device such as an ICP-MS device or an AAS device.

Figure 2:
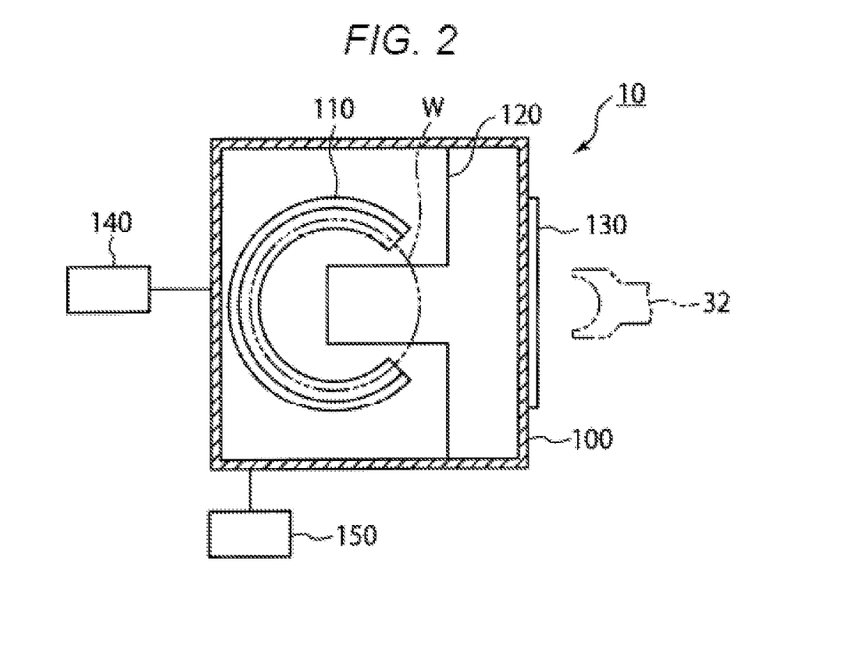
FIG. 2 is a cross-sectional view illustrating an example of a configuration of a vapor phase decomposition unit.

FIG. 2 is a cross-sectional view illustrating an example of a configuration of the vapor phase decomposition unit 10. FIG. 2 illustrates a cross-section viewed from the top of a surface of a stage 110 on which the substrate W is mounted. In some embodiments, the vapor phase decomposition unit 10 includes a chamber 100, the stage 110, a partition plate 120, a carry-in port 130, a processing gas supply unit 140, and an evacuation pump 150. In some embodiments, the vapor phase decomposition unit 10 can perform vapor phase decomposition of the material film on the substrate W by using processing gas.

In some embodiments, the chamber 100 can contain the substrate W which is carried in from the carry-in port 130. The chamber 100 uses, for example, polytetrafluoroethylene (PTFE). In some embodiments, the inside of the chamber 100 can be depressurized by the evacuation pump 150 which is a depressurization unit. In some embodiments, the substrate W may include a material film (not illustrated) which is an analysis target on a front surface thereof.

In some embodiments, the stage 110 may be provided to be able to mount the substrate W in the chamber 100. In some embodiments, the stage 110 is fixed in the chamber 100 through the partition plate 120 protruding from a side wall of the chamber 100 in a horizontal direction. In some embodiments, the partition plate 120 may have a notch such that a robot arm 32 of the transport unit 50 does not interfere. Thereby, in some embodiments, the recovery unit 30 can mount the substrate W on the stage 110 by carrying in the substrate into the chamber 100 through the carry-in port 130, and can carry the substrate W from the stage 110 to the outside of the chamber 100.

In some embodiments, the processing gas supply unit 140 can introduce processing gas which decomposes the material film (for example, a silicon oxide film, a silicon nitride film, a silicon oxynitride film, or the like) on the substrate W into the chamber 100. In some embodiments, the processing gas can dissolve a material film, and, for example, may be a gas containing fluorine in which gaseous hydrofluoric acid and gaseous water are mixed together. In some embodiments, a cleaning liquid supply pipe through which cleaning liquid (for example, pure water) for cleaning the front surface of the substrate W is supplied, an inert gas supply pipe through which inert gas (for example, nitrogen) is supplied into the chamber 100, and an evacuation pipe (not illustrated) through which gas in the chamber 100 is evacuated may be provided. Thereby, in some embodiments, the vapor phase decomposition unit 10 can purge the processing gas by introducing the inert gas such as nitrogen.

Figure 3A:
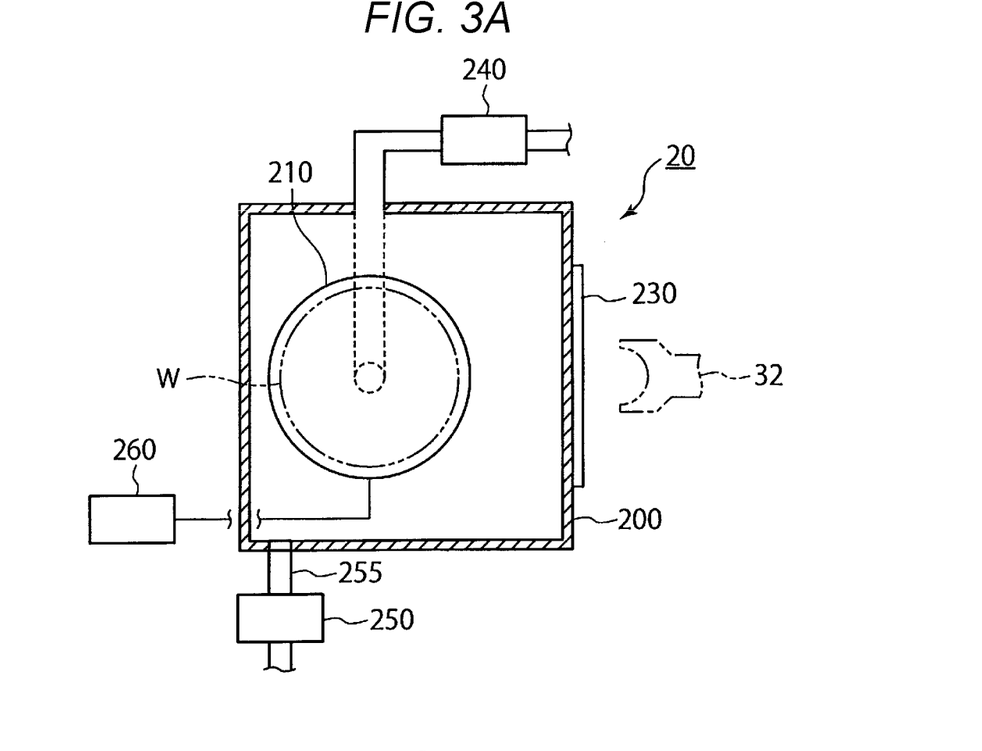
FIG. 3A and FIG. 3B are cross-sectional views illustrating an example of a configuration of a heating unit.
Figure 3B:
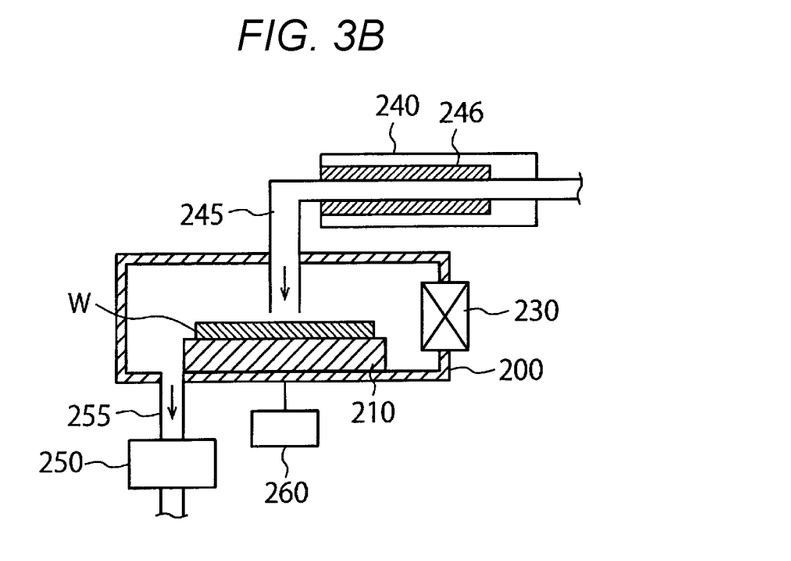

FIG. 3A and FIG. 3B are cross-sectional views illustrating an example of a configuration of the heating unit 20. FIG. 3A illustrates a cross-section viewed from the top of a surface of a stage 210 on which the substrate W is mounted, and FIG. 3B illustrates a cross-section viewed from a side of the stage 210.

The heating unit 20 includes a chamber 200, the stage 210, a carry-in port 230, an inert gas supply unit 240, a gas supply pipe 245, an evacuation pump 250, an evacuation pipe 255, and a controller 260. The heating unit 20 thermally decomposes decomposition product remaining on the front surface of the substrate W by heating the substrate W.

In some embodiments, the chamber 200 can contain the substrate W carried in from the carry-in port 230. The chamber 200 uses, for example, PTFE. In some embodiments, the inside of the chamber 200 can be depressurized by the evacuation pump 250.

In some embodiments, after the vapor phase decomposition is processed, the substrate W may include decomposition product (not illustrated) on a front surface thereof. For example, in a case where a material film on the substrate W is a silicon oxide film, a silicon nitride film, or a silicon oxynitride film, the decomposition product may contain a silicon compound such as ammonium silicofluoride (($NH_4$)$_2SiF_6$). In some embodiments, in a case where metal impurities are contained in the material film, the metal impurities may remain on the substrate W together with the decomposition product. The metal impurities include, for example, copper (Cu), iron (Fe), nickel (Ni), zirconium (Zn), ruthenium (Ru), or the like.

In some embodiments, the stage 210 is provided to be able to mount the substrate W in the chamber 200. In some embodiments, the stage 210 may be a hot plate which can heat the substrate W in a state where the substrate W is mounted. In some embodiments, the stage 210 can heat the substrate W, thereby thermally decomposing the decomposition product on the substrate W, so that the decomposition product is removed. In some embodiments, the stage 210 is larger than the substrate W and can perform approximately uniform heating of the entire substrate W. In some embodiments, temperatures of the stage 210 and the substrate W may be controlled by the controller 260. For example, the controller 260 can heat the stage 210 to the temperature of approximately 160° C., and heat the substrate W on the stage 210 (e.g., hot plate) to the temperature of approximately 160° C. Thereby, in some embodiments, the decomposition product on the substrate W can be thermally decomposed, thereby removing the decomposition product. In some embodiments, the heating unit 20 may heat the substrate by using the stage 210 as a hot plate, but may heat the substrate W by using, e.g., infrared rays or the like of an infrared lamp (not illustrated) or the like. In some embodiments, the controller 260 controls the infrared lamp.

In some embodiments, the inert gas supply unit 240 is connected to the chamber 200 through the gas supply pipe 245, and can supply inert gas to the chamber 200. In some embodiments, the inert gas supply unit 240 can supply the inert gas onto the front surface of the substrate W. The inert gas may be, for example, nitrogen or the like. In some embodiments, the inert gas supply unit 240 includes a heater 246 illustrated in FIG. 3B, which heats the inert gas such that temperature of the inert gas is approximately equal to the temperature of the heated substrate W. In some embodiments, the inert gas supply unit 240 can introduce the heated inert gas into the chamber 200. Thereby, in some embodiments, the temperature of the substrate W can be stabilized, and thus, it is possible to prevent the progress of the thermal decomposition of the decomposition product from being impeded by introducing the inert gas.

The evacuation pump 250 and the evacuation pipe 255 which function as an evacuation unit are connected to the bottom of the chamber 200, and evacuate gas in the chamber 200 to an outside of the chamber 200. In some embodiments, the evacuation pump 250 can evacuate the gas from the chamber 200 through the evacuation pipe 255. Thereby, in some embodiments, the thermally decomposed decomposition product can be evacuated to an outside of the chamber 200 without remaining in the chamber 200 for a long time. In some embodiments, the evacuation pump 250 can evacuate the inert gas introduced into the chamber 200 from the inert gas supply unit 240, from the chamber 200.

Figure 4:
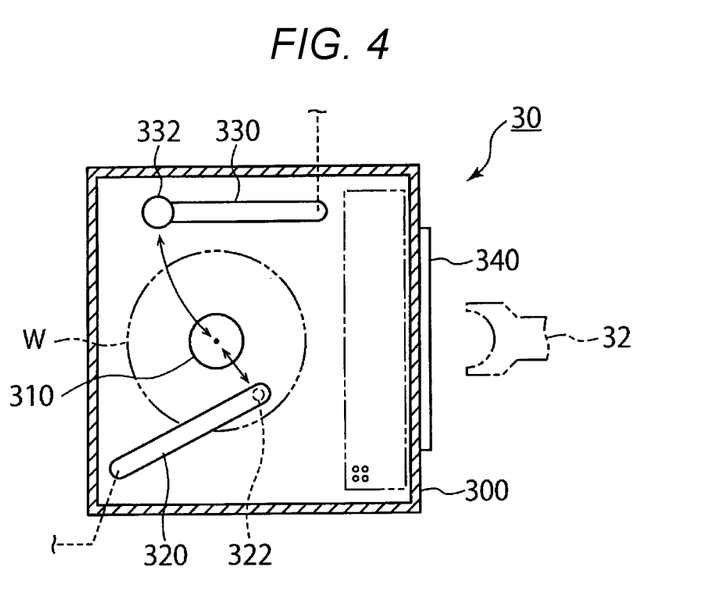
FIG. 4 is a cross-sectional view illustrating an example of a configuration of a recovery unit.

FIG. 4 is a sectional view illustrating an example of a configuration of the recovery unit 30. In some embodiments, the recovery unit 30 includes a chamber 300, a stage 310, a recovery solution moving unit 320, a recovery solution drying unit 330, and a carry-in port 340. In some embodiments, the recovery unit 30 can recover the object to be measured to analyze the remaining object to be measured (e.g., metal impurities) after the vapor phase decomposition unit 10 performs vapor phase decomposition of the material film. In some embodiments, the recovery solution drying unit 330 may be provided in a case where the analysis unit 40 uses a TXRF analysis device. In some embodiments, the recovery solution drying unit 330 is not provided in a case where the analysis unit 40 uses an ICP-MS device or an AAS device.

In some embodiments, a chamber 300 can contain the substrate W carried in from the carry-in port 340, and can use, for example, PTFE. In some embodiments, the robot arm 32 can transport the substrate W from the heating unit 20 to the recovery unit 30 after heat processing is performed. In some embodiments, the robot arm 32 can carry in the substrate W into the chamber 300 through the carry-in port 340.

In some embodiments, the stage 310 is provided in the chamber 300 such that the substrate W can be mounted. In some embodiments, the stage 310 can rotate the substrate W while retaining the approximately horizontal substrate.

In some embodiments, a nozzle 322 is provided at one end of the recovery solution moving unit 320. In some embodiments, the other end of the recovery solution moving unit 320 is connected to a shaft (not illustrated), and is configured to be rotatable around the shaft. In some embodiments, as the recovery solution moving unit 320 rotates around the shaft, the nozzle 322 can be moved in an approximately horizontal state between an end of the substrate W and the center of the substrate W. In some embodiments, the nozzle 322 can supply a recovery solution onto the front surface of the substrate W and retains the recovery solution. In some embodiments, the front surface of the substrate W may have hydrophobicity, such that the recovery solution does not flow from the direct bottom of the nozzle 322, and can be retained between the nozzle 322 and the substrate W. In some embodiments, the recovery solution moving unit 320 can supply the recovery solution onto the front surface of the substrate W, and move the recovery solution from the end portion of the substrate W to the center thereof while rotating the substrate W. Thereby, in some embodiments, the recovery solution can scan the entire front surface of the substrate W, so that the object to be measured (metal impurities) existing on the front surface of the substrate W can be recovered into the center of the substrate W. The recovery solution may be, for example, a mixed aqueous solution of hydrofluoric acid of approximately 2% and hydrogen peroxide water of approximately 2%, or a mixed aqueous solution of hydrofluoric acid of approximately 1% and hydrogen peroxide water of approximately 3%. In some embodiments, the recovery solution may be, for example, a mixed aqueous solution of hydrofluoric acid, hydrochloric acid, and water, a mixed aqueous solution of hydrochloric acid and aqueous hydrogen peroxide, or a mixed aqueous solution of nitric acid, hydrochloric acid, and hydrofluoric acid.

In some embodiments, a lamp 332 which heats the recovery solution by irradiating the recovery solution on the substrate W with light is provided at one end of the recovery solution drying unit 330. In some embodiments, the other end of the recovery solution drying unit 330 is connected to a shaft (not illustrated), and is configured to be rotatable around the shaft. In some embodiments, as the recovery solution drying unit 330 rotates around the shaft, the lamp 332 can be moved in an approximately horizontal state between the end and the center of the substrate W. The lamp 332 is, for example, an infrared lamp. Thereby, in some embodiments, the recovery solution drying unit 330 dries the object to be measured by heating the recovery solution in which the object to be measured is recovered, using the lamp 332. In some embodiments, the recovery solution drying unit 330 may dry the recovery solution by using a heating unit other than the lamp.

In some embodiments, the recovery unit 30 can perform analysis by using a TXRF method, and thereby, the recovery solution drying unit 330 can dry the recovery solution at a central portion of the substrate W. In some embodiments, in a case where analysis is performed by using an ICP-MS method or an AAS method, the recovery solution drying unit 330 is not provided, and the recovery solution may be transported in the state of liquid to an analysis unit (not illustrated) which uses the ICP-MS method or the AAS method. In some embodiments, since the solution needs not be dried at the center of the substrate W, the nozzle 322 may scan the substrate W from an outer circumference to the center.

In the analysis device 1 according to some embodiments, when the decomposition product (e.g., silicon compound) generated by the vapor phase decomposition is thermally decomposed, the heating unit 20 can heat the substrate W while gas in the chamber 200 is evacuated. Thereby, in some embodiments, gas which is generated by thermally decomposing the decomposition product can be evacuated from the chamber 200, and it is possible to prevent the decomposition product from being deposited on an inner wall of the chamber 200 and each member of the heating unit 20. As a result, in some embodiments, the analysis device 1 can prevent the decomposition product from dropping or being reattached to the substrate W, and can analyze easily and accurately the metal impurities in the material film.

In some embodiments, the heating unit 20 includes the inert gas supply unit 240, and evacuates gas in the chamber 200 while supplying inert gas. Thereby, in some embodiments, it is possible to smoothly and efficiently evacuate the decomposition product which is decomposed in the chamber 200 to an outside of the chamber 200, and to prevent the decomposition product from being deposited on the inner wall of the chamber 200 and each member of the heating unit 20. In some embodiments, the inert gas with approximately the same temperature as the temperature of the heated substrate W may be introduced into the chamber 200. Thereby, in some embodiments, temperature of the substrate W can be stabilized, and thus, it is possible to prevent the progress of the thermal decomposition of the decomposition product from being impeded by introducing the inert gas.

Next, an operation of the analysis device 1 according to some embodiments will be described.

Figure 5:
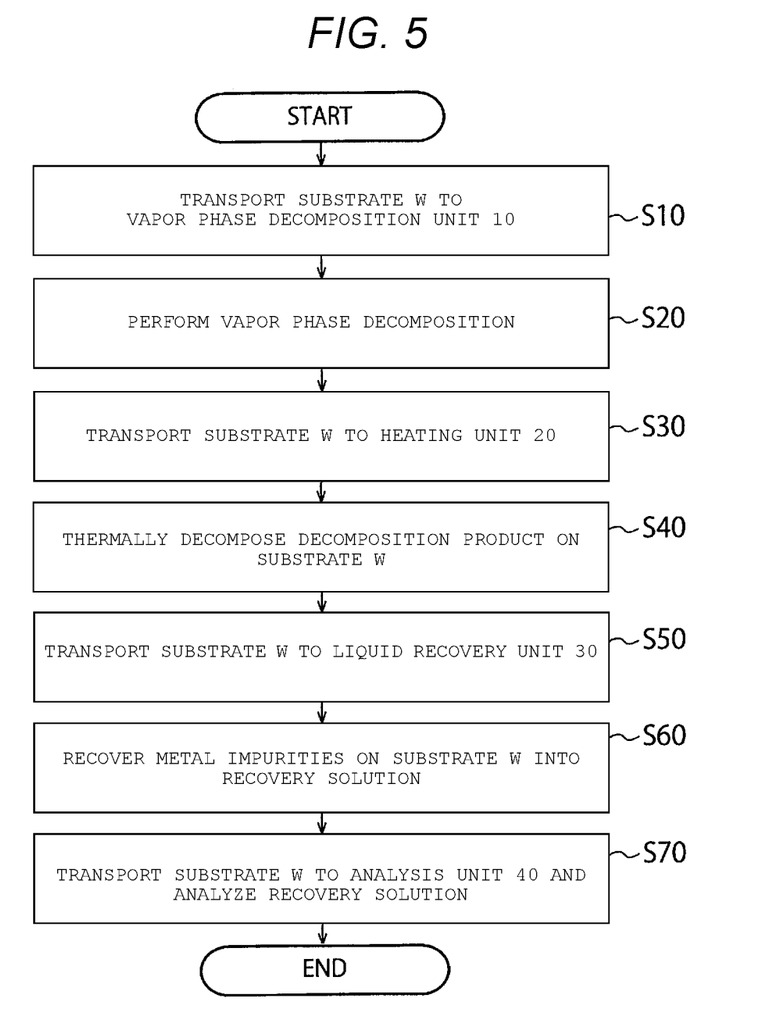
FIG. 5 is a flowchart illustrating an example of an operation of the analysis device according to some embodiments.

FIG. 5 is a flowchart illustrating an example of the operation of the analysis device 1 according to some embodiments.

In some embodiments, an analysis target is, for example, a silicon nitride film formed on a semiconductor substrate.

First, in some embodiments, the substrate W is transported to the vapor phase decomposition unit 10 and is mounted on the stage 110 (S10).

Subsequently, in some embodiments, the processing gas supply unit 140 introduces processing gas into the chamber 100. The processing gas is, for example, hydrofluoric acid vapor. In some embodiments, the hydrofluoric acid vapor can be generated by performing $N_2$ bubbling to commercially available hydrofluoric acid. In some embodiments, the hydrofluoric acid vapor may be introduced into the chamber 100 by spraying hydrofluoric acid by using a nebulizer. In some embodiments, by introducing the hydrofluoric acid vapor into the chamber 100, the inside of the chamber 100 is filled with hydrofluoric acid vapor, and vapor phase decomposition of a silicon nitride film is performed (S20). In some embodiments, if the vapor phase decomposition of the silicon nitride film is performed, a large amount of decomposition product (silicon compound) may be extracted on the substrate W.

In some embodiments, after the vapor phase decomposition of the silicon nitride film is performed, nitrogen gas may be supplied into the chamber 100, and may purge the inside of the chamber 100. In some embodiments, gas which is used for purging the chamber 100 may be clean dry air not containing a metal or inert gas other than nitrogen. In some embodiments, if an HF gas detector (not illustrated) is used, it is possible to detect that evacuation of hydrofluoric acid vapor is completed.

Subsequently, in some embodiments, the substrate W is transported to the heating unit 20, and is mounted on the stage 210 (S30). For example, the substrate W is heated on the stage 210 heated to approximately 160° C. Thereby, in some embodiments, the decomposition product (silicon compound such as ammonium silicofluoride) on the substrate W is thermally decomposed and is removed (S40). At this time, in some embodiments, the stage 210 may heat the substrate W as a hot plate. In some embodiments, the substrate W may be heated from above by irradiating the substrate W with infrared rays, using an infrared lamp.

Here, in some embodiments, the substrate W on the stage 210 is heated and the evacuation pump 250 evacuates gas in the chamber 200 through the evacuation pipe 255. Thereby, in some embodiments, the thermally decomposed decomposition product can be evacuated to an outside of the chamber 200. In some embodiments, the inert gas introduced into the chamber 200 from the inert gas supply unit 240 can also be evacuated from the inside of the chamber 200 by the evacuation pump 250. In some embodiments, as the inert gas is introduced, the thermally decomposed decomposition product can be smoothly evacuated from the chamber 200. For example, the inert gas supply unit 240 supplies nitrogen gas from above the central portion of the substrate W at a flow rate of approximately 10 L (liters)/min. Meanwhile, the evacuation pump 250 evacuate gas from the chamber 200 at a flow rate (for example, approximately 20 L (liters)/min) higher than the flow rate of the nitrogen gas from the inert gas supply unit 240. Thereby, in some embodiments, the decomposition product which is thermally decomposed on the substrate W is evacuated from the chamber 200 together with the nitrogen gas without being attached to the front surface of the substrate W and the inner wall of the chamber 200. In some embodiments, the flow rate of the nitrogen gas from the inert gas supply unit 240 can be controlled by a feedback control system which uses a flow meter and a regulator.

In some embodiments, the heater 246 of the inert gas supply unit 240 supply inert gas with temperature which is approximately equal to temperature of the stage 210 and the substrate W. For example, in a case where the stage 210 heats the substrate W to the temperature of approximately 160° C., the heater 246 supplies nitrogen gas with temperature of approximately 160° C. to the substrate W. Thereby, in some embodiments, the temperature of the stage 210 and the substrate W is stabilized, and thus, it is possible to prevent the progress of the thermal decomposition of the decomposition product from being impeded by introducing the inert gas.

In some embodiments, the heat decomposition processing of the substrate W may be performed by the vapor phase decomposition unit 10. In some embodiments, the vapor phase decomposition unit 10 and the heating unit 20 may be combined to be one piece. In this case, in some embodiments, the vapor phase decomposition unit 10 and the heating unit 20 are provided within a common chamber (see the dotted line in FIG. 1). In some embodiments, the stage 110 of the vapor phase decomposition unit 10 may be a hot plate which can heat the entire substrate W like the stage 210 of the heating unit 20. In some embodiments, the vapor phase decomposition unit 10 may include an infrared lamp which can heat the substrate W.

Subsequently, in some embodiments, after the substrate W is lifted from the stage 210 by a lift pin or the like and is cooled, the substrate W is transported to the recovery unit 30, and is mounted on the stage 310 (S50). In some embodiments, a recovery solution is dropped on the substrate W by approximately 0.1 ml, the entire front surface of the substrate W is scanned by the recovery solution, and metal impurities on the substrate W are recovered into the recovery solution (S60). For example, the recovery solution uses a mixed solution of hydrofluoric acid of approximately 2% and hydrogen peroxide water of approximately 2%. In some embodiments, in a case where the mixed solution of hydrofluoric acid and hydrogen peroxide water has low recovery efficiency of metal impurities, a mixed aqueous solution of hydrofluoric acid, hydrochloric acid, and water, a mixed solution of hydrochloric acid and hydrogen peroxide solution, or a mixed aqueous solution of nitric acid, hydrochloric acid, and hydrofluoric acid may be used as the recovery solution.

Subsequently, in some embodiments, the substrate W may be transported to the analysis unit 40. In some embodiments, after the recovery solution is dried in which the metal impurities are dissolved by using a lamp by the recovery unit 30, the substrate W is analyzed by using the TXRF method (S70). In some embodiments, the analysis unit 40 analyzes contents of a material film by irradiating a dry mark obtained by drying the recovery solution on the substrate W with an X-ray. In some embodiments, the recovery solution may be analyzed as it is by using the ICP-MS method or the AAS method, without drying. Thereby, in some embodiments, a type, the amount of containment, and the like of the metal impurities which are contained in the silicon nitride film can be confirmed.

As described above, in the analysis device 1 according to some embodiments, when the decomposition product on the substrate W is thermally decomposed, the heating unit 20 can heat the substrate W while gas in the chamber 200 is evacuated. Thereby, in some embodiments, gas which is generated by thermally decomposing the decomposition product can be evacuated from the chamber 200, and it is possible to prevent the decomposition product from being deposited on an inner wall of the chamber 200 and each member of the heating unit 20. In some embodiments, the heating unit 20 evacuates gas in the chamber 200 while supplying inert gas. Thereby, in some embodiments, the decomposition product decomposed in the chamber 200 can be smoothly and efficiently evacuated to an outside of the chamber 200, and it is possible to prevent the decomposition product from being deposited on the inner wall of the chamber 200 and each member of the heating unit 20. As a result, the analysis device 1 can prevent the decomposition product from dropping or being reattached to the substrate W, and can analyze easily and accurately the metal impurities in the material film. In some embodiments, inert gas may be introduced into the chamber 200 at approximately the same temperature as the heated temperature of the substrate W. Thereby, in some embodiments, the temperature of the substrate W can be stabilized, and thus, the thermal decomposition of the decomposition product can be smoothly performed.

Figure 6A:
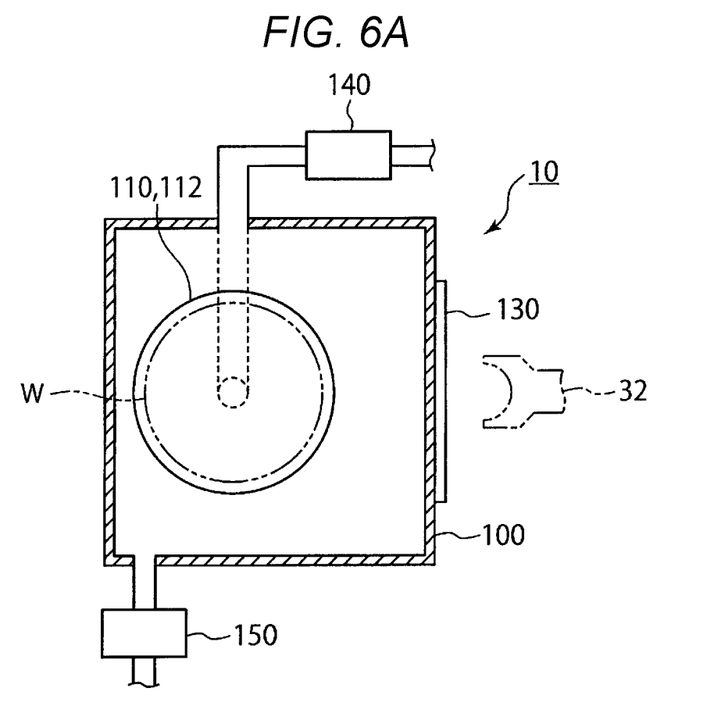
FIG. 6A and FIG. 6B are cross-sectional views illustrating an example of a configuration of the vapor phase decomposition unit of the analysis device according to some embodiments.
Figure 6B:
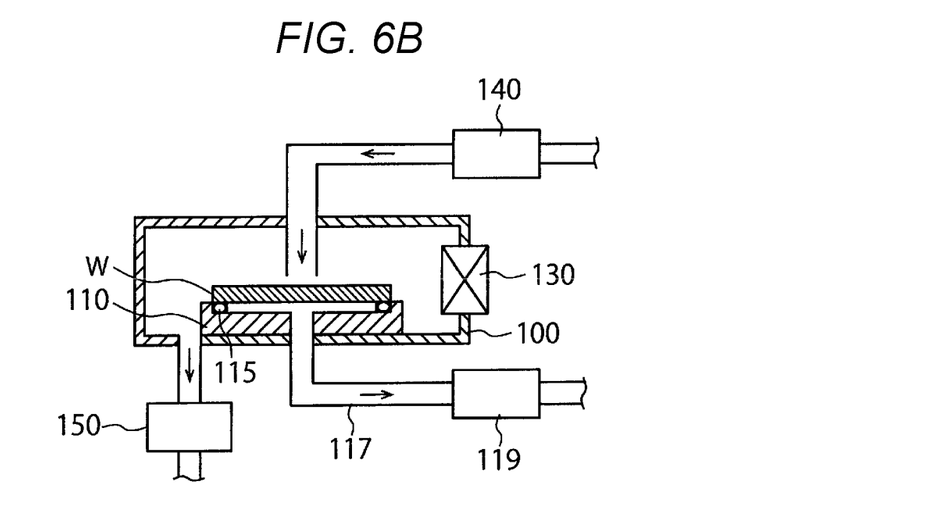

FIG. 6A and FIG. 6B are cross-sectional views illustrating an example of a configuration of the vapor phase decomposition unit 10 of the analysis device 1 according to some embodiments. FIG. 6A illustrates a cross-section viewed from the top of a surface of the stage 110 on which the substrate W is mounted, and FIG. 6B illustrates a cross-section viewed from a side of the stage 110.

The vapor phase decomposition unit 10 according to some embodiments includes a packing 115, a suction pipe 117, and a suction pump 119. The packing 115, the suction pipe 117, and the suction pump 119 function as an adsorption unit which adsorbs a rear surface of the substrate W.

In some embodiments, the packing 115 is provided on the stage 110 so as to correspond to an outer circumference of the substrate W. In some embodiments, when the substrate W is mounted on the stage 110, the packing 115 can seal a space between the rear surface of the substrate W and the stage 110. For example, a fluorine resin can be used for the packing 115.

In some embodiments, the suction pipe 117 is a conduit which connects the stage 110 to the suction pump 119. In some embodiments, the suction pump 119 can apply suction to gas between the substrate W and the stage 110 through the suction pipe 117. Thereby, in some embodiments, the suction pipe 117 and the suction pump 119 can apply suction to the gas from the space between the rear surface of the substrate W and the stage 110 which are sealed by the packing 115, thereby being able to make the substrate W be adsorbed to the stage 110.

In some embodiments, the stage 110 has an outer circumference greater than the outer circumference of the substrate W, and the substrate W can be mounted on the stage. In some embodiments, since an adsorption unit 112 adsorbs the entire rear surface of the substrate W, a lift pin (not illustrated) which lifts the substrate W can be provided in the stage 110 such that the robot arm 32 does not interfere with the stage 110. Other configurations according to some embodiments may be the same as the configuration corresponding to the embodiments illustrated in 1-5.

In some embodiments, as the packing 115, the suction pipe 117, and the suction pump 119 which function as an adsorption unit adsorb the rear surface of the substrate W, it is possible to prevent processing gas (for example, hydrofluoric acid vapor) from entering the rear surface side of the substrate W.

In some embodiments, if vapor phase decomposition of a material film on the rear surface side of the substrate W is performed, decomposition product is attached to the rear surface of the substrate W. Since the decomposition product on the rear surface of the substrate W is not recovered, when the substrate W is transported to the substrate container 60 illustrated in FIG. 1, the decomposition product is attached to the inside of the substrate container 60. Thereafter, the decomposition product attached to the substrate container 60 can be attached to other substrates W.

In some embodiments, the packing 115, the suction pipe 117, and the suction pump 119 can adsorb the rear surface of the substrate W and prevent the processing gas from entering the rear surface of the substrate W. Thereby, in some embodiments, the decomposition product can be prevented from being attached to the rear surface of the substrate W. As a result, it is possible to prevent the decomposition product from being attached to the substrate container 60, or to prevent the decomposition product from being attached to other substrates W in the substrate container 60. Furthermore, the embodiments illustrated in FIG. 6A and FIG. 6B may have the same effects as the embodiments illustrated in FIGS. 1-5.

In some embodiments, the adsorption unit may be an electrostatic chuck which adsorbs the rear surface of the substrate W by using static electricity. In some embodiments, a potential control unit (not illustrated) which supplies a potential to the stage 110 is provided instead of the packing 115, the suction pipe 117, and the suction pump 119. In some embodiments, the potential control unit supplies a predetermined potential to the stage 110 such that the substrate W is electrically adsorbed to the stage 110.

In some embodiments, in order to prevent processing gas from entering a rear surface side of the substrate W, dry air or inert gas may be sprayed onto the rear surface of the substrate W. Thereby, in some embodiments, the decomposition product can also be prevented from being attached to the rear surface of the substrate W.

Figure 7:
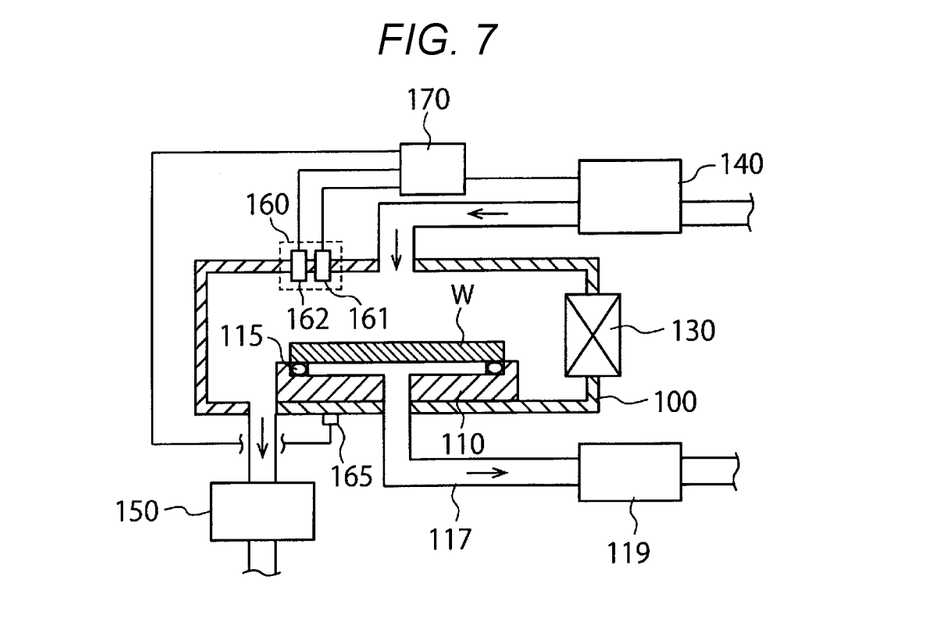
FIG. 7 is a cross-sectional view illustrating an example of a configuration of the vapor phase decomposition unit of the analysis device according to some embodiments.

FIG. 7 is a sectional view illustrating an example of a configuration of the vapor phase decomposition unit 10 of the analysis device 1 according to some embodiments. The vapor phase decomposition unit 10 according to some embodiments further includes sensing units 160 and 165 which sense a material film on the substrate W, and a determination unit 170 which determines an end point of vapor phase decomposition of the material film on the basis of the sensing results of the sensing units.

In some embodiments, the sensing unit may be a reflectance ratio measuring device 160 which measures a reflectance ratio of the substrate W or the material film by irradiating the substrate W or the material film with light. In some embodiments, the sensing unit may be a weight sensor 165 which measures weight of the substrate W.

In some embodiments, the reflectance ratio measuring device 160 includes a light emitting unit 161 and a light receiving unit 162. In some embodiments, the light emitting unit 161 emits light (for example, ultraviolet rays) toward the substrate W. In some embodiments, the light receiving unit 162 measures intensity of the reflected light from the substrate W or the material film. In some embodiments, reflectance ratio can be calculated from a ratio between emitted light intensity of the light emitting unit 161 and reflected light intensity of the light receiving unit 162. In some embodiments, the reflectance ratio may be calculated by the determination unit 170.

In some embodiments, the weight sensor 165 is provided in the stage 110, and can measure a weight of the substrate W.

In some embodiments, the determination unit 170 can compare the sensing results (for example, reflectance ratio of the material film and weight of the substrate W) with a threshold, and determine an end point of vapor phase decomposition of the material film. For example, in a case where the reflectance ratio is approximately equal to the threshold (reflectance ratio of the substrate W), the determination unit 170 determines that the vapor phase decomposition of the material film ends. In some embodiments, in a case where the weight of the substrate W is less than a threshold, the determination unit 170 determines that the vapor phase decomposition of the material film ends. In some embodiments, the thresholds may be stored in advance in a memory (not illustrated) provided in the analysis device 1. In some embodiments, the thresholds may be input from the outside of the analysis device 1. In some embodiments, the determination unit 170 may be implemented using a central processing unit or an electronic circuit. Other configurations according to some embodiments may be the same as configurations corresponding to the configuration of the embodiments illustrated in FIGS. 1-5.

Figure 8:
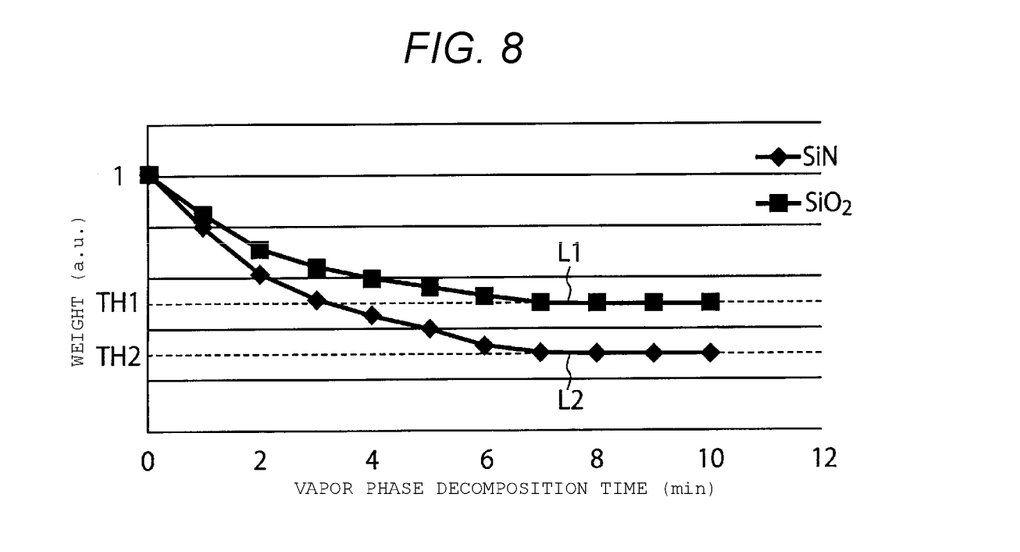
FIG. 8 is a graph illustrating a relationship between a vapor phase decomposition time and a weight of a substrate.

FIG. 8 is a graph illustrating a relationship between the vapor phase decomposition time and the weight of the substrate W. A horizontal axis denotes the weight of the substrate W, and a vertical axis denotes the vapor phase decomposition time. The graph illustrates a change of the weight of the substrate W, assuming that the weight of the substrate W is one when the vapor phase decomposition time is zero. A line L1 denotes a weight in a case where the material film is a silicon oxide film. A line L2 denotes a weight in a case where the material film is a silicon nitride film.

For example, in a case where the material film is a silicon oxide film, when the weight of the substrate W is less than a threshold TH1, the determination unit 170 determines that vapor phase decomposition of the film ends, and automatically stop supplying of processing gas. In some embodiments, in a case where the material film is a silicon nitride film, when the weight of the substrate W is less than a threshold TH2, the determination unit 170 determines that vapor phase decomposition of the film ends, and automatically stop supplying of processing gas. As such, in some embodiments, in a case where an end point of the vapor phase decomposition is determined by using the weight sensor 165, when the weight of the substrate W is less than a threshold, the determination unit 170 determines that the vapor phase decomposition of the material film ends. In some embodiments, since the determination of the end point of the vapor phase decomposition which is performed by using the reflectance ratio measuring device 160 can be easily assumed from an example of the determination of the end point of the vapor phase decomposition which is performed by using the weight sensor 165, detailed description thereof is omitted.

In some embodiments, in a case where it is determined that the vapor phase decomposition of the material film ends, the determination unit 170 controls the processing gas supply unit 140 to automatically stop supplying of the processing gas. Thereby, it is possible to prevent the processing gas from being oversupplied to the chamber 100 by the processing gas supply unit 140. In other words, it is possible to prevent supplying of the processing gas from being stopped by the processing gas supply unit 140, although the material film remains on the substrate W.

In some embodiments, in a case where the processing gas is supplied only for a predetermined time (for example, 10 minutes), although the material film remains on the substrate W, the processing gas supply unit 140 stops supplying of the processing gas if the predetermined time elapses after supplying of the processing gas starts. If the material film remains on the substrate W, the material film (for example, silicon nitride film) is not thermally decomposed. Thus, metal impurities of the material film cannot be recovered to a recovery solution.

The analysis device 1 according to some embodiments senses presence or absence of a material film on the substrate W, and determines an end point of vapor phase decomposition of the material film on the basis of the sensed results. Thereby, in some embodiments, after the vapor phase decomposition of the entire material film is performed, the processing gas supply unit 140 can stop supplying of processing gas. As a result, it is possible to recover metal impurities included in the entire metal impurities into a recovery solution.

In some embodiments as shown in FIG. 7, the vapor phase decomposition unit 10 includes both the reflectance ratio measuring device 160 and the weight sensor 165. Thereby, in some embodiments, the end point of the vapor phase decomposition of the material film is accurately sensed. In some embodiments, the vapor phase decomposition unit 10 may include any one of the reflectance ratio measuring device 160 and the weight sensor 165.

The embodiments illustrated in FIG. 7 and FIG. 8 may have the same effects as the embodiments illustrated in FIGS. 1-5. The embodiments illustrated in FIG. 7 and FIG. 8 may be combined with the embodiments illustrated in FIG. 6A and FIG. 6B. Thereby, the embodiments illustrated in FIG. 7 and FIG. 8 can also obtain the effects of the embodiments illustrated in FIG. 6A and FIG. 6B.

In the description of some embodiments, two numerical values can be deemed to be "approximately" the same or equal if a difference between the values is less than or equal to ±10% of an average of the values, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

While certain embodiments have been described, these embodiments have been presented by way of example only, and are not intended to limit the scope of the present disclosure. Indeed, the embodiments described herein may be embodied in a variety of other forms; furthermore, various omissions, substitutions and changes in the form of the embodiments described herein may be made without departing from the spirit of the present disclosure. The accompanying claims and their equivalents are intended to cover such forms or modifications as would fall within the scope and spirit of the present disclosure.

What is claimed is:

1. An analysis device comprising:
   a vapor phase decomposition chamber configured to perform vapor phase decomposition of a first film on a front surface of a substrate;

a first evacuation pump configured to evacuate gas in the vapor phase decomposition chamber to an outside of the vapor phase decomposition chamber;

a heating chamber configured to heat the substrate;

a second evacuation pump configured to evacuate gas in the heating chamber to an outside of the heating chamber;

a recovery chamber configured to supply liquid on the front surface of the substrate, move the liquid on the front surface of the substrate, and recover the liquid; and an analyzer configured to analyze a containing metal material in the liquid, wherein the heating chamber comprising a hot plate being able to heat the substrate performed vapor phase decomposition by the vapor phase decomposition chamber in a state where the substrate is mounted.

2. The device according to claim 1, further comprising:

a suction pipe configured to adsorb a rear surface of the substrate in an inside of vapor phase decomposition chamber.

3. The device according to claim 1, further comprising:

a weight sensor configured to measure a weight of the substrate in the vapor phase decomposition chamber; and a processor configured to determine an end point of vapor phase decomposition of the first film on the basis of a weight of the substrate.

4. The device according to claim 1, further comprising:

a reflectance ratio measuring device configured to measure a reflectance ratio of the substrate or the first film by irradiating the substrate or the first film with light from the vapor phase decomposition chamber; and a processor configured to determine an end point of vapor phase decomposition of the first film on the basis of the reflectance ratio of the substrate or the first film.

5. The device according to claim 1, further comprising:

a supplier and configured to supply an inert gas to the heating chamber.

6. The device according to claim 5, wherein the second evacuation pump is further configured to evacuate gas which is thermally decomposed in the substrate together with the inert gas.

7. The device according to claim 5, wherein a temperature of the inert gas is approximately equal to a temperature of the substrate heated in the heating chamber.

8. The device according to claim 1, wherein the vapor phase decomposition chamber and the heating chamber are provided in a common chamber.

9. The device according to claim 1, wherein the vapor phase decomposition unit chamber comprising a first carry-in port from which the substrate is carried in.

10. The device according to claim 1, wherein the heating chamber comprising a second carry-in port from which the substrate is carried in after the vapor phase decomposition.

11. The device according to claim 1, wherein the analyzer is a total reflection X-ray fluorescence (TXRF) device.

12. The device according to claim 1, wherein the analyzer is an inductively coupled plasma-mass spectrometry (ICP-MS) device.

13. The device according to claim 1, wherein the analyzer is an atomic absorption spectrometry (AAS) device.

14. The device according to claim 1, wherein the recovery chamber is configured to supply liquid on the front surface of the substrate heated by the heating chamber, move the liquid on the front surface of the substrate, and recover the liquid.

15. The device according to claim 1, wherein the second evacuation pump is configured to evacuate the gas after the vapor phase decomposition of the first film.

* * * * *